United States Patent [19]

Davidson

[11] Patent Number: 5,320,098
[45] Date of Patent: Jun. 14, 1994

[54] OPTICAL TRANSDERMAL LINK

[75] Inventor: Howard L. Davidson, San Carlos, Calif.

[73] Assignee: Sun Microsystems, Inc., Mountain View, Calif.

[21] Appl. No.: 963,654

[22] Filed: Oct. 20, 1992

[51] Int. Cl.$^5$ ............................................. A61B 5/00
[52] U.S. Cl. ..................................... 128/630; 128/908
[58] Field of Search ......... 128/630, 633, 697, 419 PG, 128/419 PT, 419 PS, 908, 607

[56] References Cited

U.S. PATENT DOCUMENTS

| | | | |
|---|---|---|---|
| 3,647,299 | 3/1972 | Lavallee | 128/633 |
| 3,672,352 | 6/1972 | Summers | 128/419 PS |
| 3,808,502 | 4/1974 | Babilos | 128/908 |
| 3,910,257 | 10/1975 | Fletcher et al. | 128/908 |
| 4,041,954 | 8/1977 | O'Hara | 128/697 |
| 4,254,776 | 3/1981 | Tanie et al. | 128/908 |
| 4,361,153 | 11/1982 | Skocum et al. | 128/419 PT |
| 4,903,701 | 2/1990 | Moore et al. | 128/419 PT |
| 4,941,201 | 7/1990 | Davis | 128/419 PG |

FOREIGN PATENT DOCUMENTS 2823931 12/1979 Fed. Rep. of Germany ...... 128/908

OTHER PUBLICATIONS

Klein et al, "IEEE Conference-Frontiers of Engineering in Healthcare", Denver, Col., Oct. 6-7, 1979, pp. 273-275.

Primary Examiner—William E. Kamm
Attorney, Agent, or Firm—Blakely Sokoloff Taylor & Zafman

[57] ABSTRACT

An optical transdermal link. The interface consists of two modules. An internal module is placed just inside the skin, and an external module is placed just outside the skin and facing the internal module. The external module is connected to a host processor via high speed serial lines. The external module contains one or two laser diodes with drivers, and one photodetector with preamplifier. The internal module contains a photocell array to provide power for itself, a photo detector, preamplifier and a clock recovery circuit for detecting the incoming signal, and a laser diode and driver for the outgoing signal. The internal module also contains modulation/demodulation and neural interface circuits peculiar to the specific application.

17 Claims, 5 Drawing Sheets

OPTICAL TRANSDERMAL LINK

BACKGROUND OF THE INVENTION

1. Field of the Invention:

This invention relates to the field of optical transmission. More particularly, this invention relates to an apparatus for transmitting energy and information optically through biological tissue.

2. Art Background:

A common method of coupling to a nervous system is to thread individual nerve fibers through ring shaped electrodes made by etching a silicon chip. This interface method is part of a class of interfaces called "chronic" neural interfaces. A chronic neural interface is a way of tapping into, at this point in the evolution of the technology, peripheral nerves in mammals. This technique has been demonstrated at Stanford University.

The Stanford device, in particular, involves integrated circuits that have had holes etched through them. A nerve is cut and a little holder for the nerve is placed across the cut end of the nerve. The nerve regenerates through the holes in the chip, providing small groups of axons in each hole. The holes have electrodes around them that allow one to drive and sense the neurons, so neural activity can be monitored and controlled. Alternative arrangements using metal and indium-tin-oxide electrodes on the surface of chips have also been demonstrated.

Alternate chronic neural interfaces are being developed elsewhere (e.g. the Veteran's Administration and the University of Michigan, Ann Arbor). Although still in the pure research stage, another such method to attach nerve cells to the chip is to induce them to grow to the electrode sites. Instead of cutting the nerves and threading them through holes, bioengineers are beginning to provide tools that allow one, with the right kind of implant, to actually request that a nerve bundle grow a tap over to a chip. This technique is much less invasive than severing a nerve.

Until recently, the dogma was that once neurons were formed in the central nervous system of mammals, no additional neurons could be formed. Epithelial growth factor has been found to stimulate division of neurons in the central nervous system of a mouse.

Using electrically sensitive polymers as a controlled long term drug delivery mechanism provides a possible way to cause a nerve bundle to grow a tap over to a chip. Small amounts of the polymer are placed at each electrode site, and the polymer is loaded with the correct mixture of cell growth factors. Stimulation of the polymer by the electrodes on the chip results in a gradient of growth factors. Under proper conditions, nerve cells will grow up the gradient, and attach themselves to the electrode site.

All electrode sites are made bi-directional, that is, each site is equipped with both drive and receive electronics. Therefore, it is possible to provide a control signal to the polymer, and to monitor for the presence of nerve cells. If each electrode site is individually controllable, one can stop driving a particular site when a nerve cell has arrived, and then drive a neighbor site to attract the next nerve cell to grow towards the chip.

The intention behind developing chronic neural interfaces is (1) to help provide a better understanding of the nervous system; and (2) to control prosthetics. The latter application helps people who have had amputations, as well as people with other problems, such as paraplegics or quadriplegics. Examples of possible prosthetic applications of this technique include hearing and vision replacement, and "jumpering" across a severed nerve to restore some amount of motor control and sensation. Thus, it is possible to reach into what is left of a damaged peripheral nerve, induce it to grow through the holes in a chip, and then extract neural signals to provide controls for an artificial arm or an artificial leg. It is also possible to provide other links. For example, it is possible to provide a link into a computer so that the computer could be controlled to provide services for a person who is paralyzed.

Furthermore, in general, it has been very difficult clinically to penetrate the skin in a long term fashion with wires or with other connectors. For example, in kidney dialysis, a vein and artery are shunted, usually in the forearm. These shunts require constant attention to prevent infections.

Therefore, for chronic neural interfaces, it is desirable to bring electrical signals in and out through the skin, but it is preferable to achieve this without using wires to penetrate the skin. Currently, the most common practice is to have signals brought in and brought out through the skin using radio transmission and reception.

It is also common to reprogram a pacemaker which has been embedded subdermally. Pacemakers are currently reprogrammed by tapping the chest with a magnet that operates a reed switch inside the pacemaker. With current technology, the reprogramming is performed at a painstakingly low data rate, in the order of bits per second. The programmer must tap with the magnet and then examine an electrocardiogram readout to determine whether the programming was performed correctly.

Simply providing power to a subdermal device is also important. For example, pacemakers currently have to be surgically removed before their batteries expire and new ones inserted. Generally, one does not want to perform surgery if it can be avoided. Therefore, it is desirable to transmit power to a subdermal site and thereby power the system.

Another current problem encountered by chronic neural interfaces is that of providing power to the subdermal chips. If there is subdermal processing circuitry that is reading, or driving the nerves, there must be electrical power for the circuitry to operate. Electrical power is most often provided by split transformer, where one half of the core of the transformer is placed inside the skin and the other half of the core is placed outside the skin. These transformers tend to be bulky objects and it is difficult to move much power through them. For example, cochlear implants are implants that are placed on the cochlea of an ear to jumper damage to either the cochlea, itself, or to repair damage that has been done to the mechanical structure of the ear and thereby bring sound to the cochlea. The cochlea is a very tight place to work, and one would prefer not be fettered by the bulk of a split transformer device.

Previous attempts to use light through the skin as the medium of bringing both power and signal in and bringing signal out have proved to be unsatisfactory. Light as a medium has not had much utility because, for people, it is desirable to place the receiving chip a little bit below the surface of the skin so that there is not an obvious lump in the person's arm (or wherever the implant is placed). However, to provide light, which is bright enough to shine through the skin, to something that is located significantly beneath the skin requires a bright light source. Alternately, one must place the external module close to the skin and align it carefully with the implant. People tend not to be very good at the performing the required alignment.

Recently, it has become quite inexpensive to generate a relatively large amount of laser light with a laser diode. A continuous wave (CW) laser diode can be used to illuminate an array of photo detectors that are connected electrically in series. A CW laser is a laser that emits energy in an uninterrupted stream rather than in spurts. These laser diodes are readily available at wavelengths between 670 nm and 1.55 μm. Wavelengths of 1.3 μm and 1.55 μm are common wavelengths that have been picked because of the utility in matching the minimum attenuation and dispersion points in optical fibers for telecommunications. If the emission wavelength of the laser is tuned to a high quantum efficiency frequency for the detector, efficiencies in excess of 50% may be realized.

The bandwidth attainable with current generation laser diodes and detectors is approximately one gigabit per second which is roughly comparable to the total bandwidth of a single human optic nerve.

A monolithic series stacked gallium arsenide (GaAs) photodiode array suitable for power reception has been demonstrated by Varian Associates, Palo Alto, Calif., for use in "power down the fiber" telephone applications. Furthermore, manufacturers, such as Laser Diode Laboratories, make a sugar cube sized laser diode, which is actually intended for soldering, that emits 10 watts of infrared light. Moreover, the current state of the art for surface emitting laser diodes is a threshold current of about 100 microamps at a forward voltage of about 1.5 volts. This represents a power consumption level of approximately 150 microwatts. Power consumption at that level is negligible when compared to the 50 to 100 milliwatts that can be delivered by an optical power transmission system.

As will be disclosed, the present invention provides an apparatus for providing power and a high speed bi-directional data link through skin tissue without requiring an electrical shunt through the skin. Signals and power are carried as infrared light.

SUMMARY OF THE INVENTION

An optical transdermal link is disclosed in which the interface is composed of two modules. An internal module is placed just inside the skin, and an external module is placed just outside the skin facing the internal module. A system using laser diodes transmits data between modules. These diodes have the capability of data transmission rates in excess of one gigabit per second. A lower cost, lower bandwidth, version uses light emitting diodes (LEDs) instead of laser diodes.

The external module contains one or two laser diodes with corresponding drivers, and one photodetector with a preamplifier. The external module is connected to a host processor which provides, via high speed serial lines, an input data stream to be transmitted to the internal module.

The internal module contains a photocell array to provide power for itself and other devices; a photo detector, preamplifier and a clock recovery circuit for detecting the incoming signal; and a laser diode and driver for transmitting a second data stream to the external module. The internal module also contains modulation/demodulation and neural interface circuits peculiar to the specific application.

There are two ways that power can be carried to the internal module. One way is to use an unmodulated laser in the external module which is dedicated solely to power transmission. A separate laser diode operating at a frequency different from the power laser diode is modulated to send the data stream. This removes the need for much internal filtering of the power at the internal module. Alternately, a trade-off may be made in the total number of laser diodes in the system by using the same external module laser diode to send both power and data to the internal module. This is accomplished by using the data stream to modulate the power beam. In this case, the high speed data photo detector of the internal module is placed in the center of the internal module power photo detector array.

A laser located in the internal module optically transmits the second data stream to the external module. The second data stream is received by a high speed photo detector located in the external module.

In general, all the laser diodes in a particular implementation will operate at different wavelengths to avoid signal crosstalk between the two signal directions. Interference filters placed over the signal photodetectors provide rejection of the other channel.

DETAILED DESCRIPTION OF THE INVENTION

Figure 1:
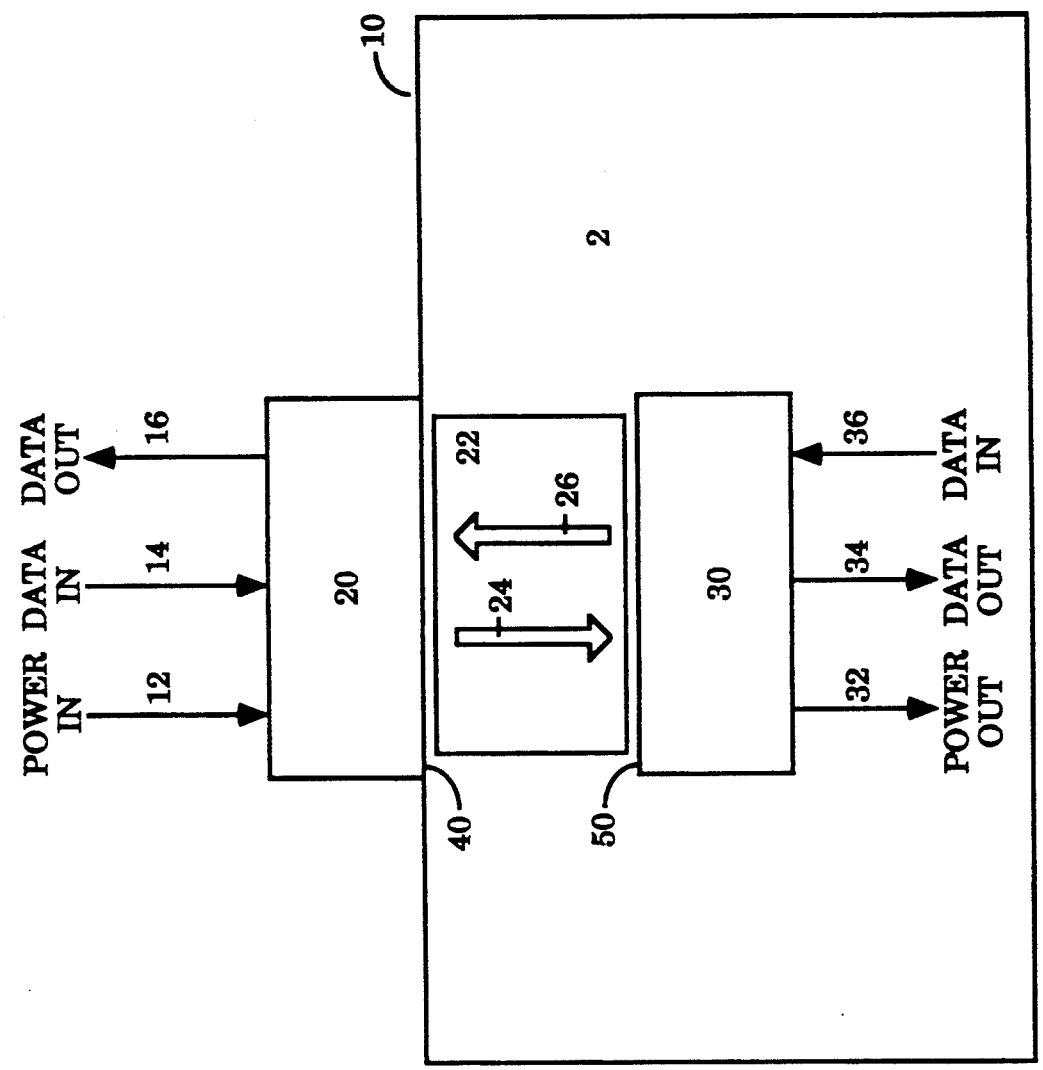
FIG. 1 illustrates one embodiment of an internal module and an external module pair which together employ the teachings of the present invention to provide an optical transdermal link.

An optical transdermal link is disclosed. In the following description, for purposes of explanation, circuit devices, circuit architectures, and components are set forth in order to provide a more thorough understanding of the present invention. However, it will be apparent to one skilled in the art that the present invention may be practiced without these specific details. In other instances, well known circuits and devices are shown in schematic form in order not to obscure the present invention unnecessarily.

It has become quite inexpensive to generate a relatively large amount of laser light with a laser diode. These laser diodes are readily available at wavelengths between 670 nm and 1.55 μm. Wavelengths of 1.3 μm and 1.55 μm are common wavelengths that have been picked because of the utility in matching the minimum attenuation and dispersion points in optical fibers for telecommunications. The present invention uses infrared light as the medium for bringing both power and data signals in through the skin and also for bringing a second data signal out through skin.

Since it lies below the band gap in the infrared range, biological tissue (e.g. skin, fat and even blood) is relatively transparent to infrared light. Therefore, infrared light can be transmitted efficiently through such biological tissue. Using an infrared laser diode, one can spread a modest amount of infrared light (approximately 100 milliwatts per square centimeter) over a one square inch (6.5 square centimeter) area of the skin surface. By distributing the light over an area, one can provide a margin for error for the placement of the light source over a receiver implanted below the skin thereby ensuring that infrared light will reach the receiver.

The power and data transmission techniques of the present invention pose little danger to skin or eyes. The skin would not be burned because the low power density required by the present invention is similar to the power density of sunlight but is at a wavelength that does not cause ultraviolet (UV) damage. Furthermore, looking at the beam would not be the same as if one were staring into a cutting beam because the power density is so low, therefore, inadvertently looking at the beam is safe. Moreover, if the laser diode emits light far enough into the infrared range, the process is also eye-safe because the cornea of the eye has no transmission in that part of the spectrum.

Since the laser diodes are supplying laser light, there is a known wavelength. One can get a large improvement in the efficiency of the electrical conversion from light to electricity by tuning photodiodes so that they have maximum absorption and maximum quantum efficiency at the wavelength being used. Therefore, instead of achieving the state of the art twelve to twenty percent power transmission efficiency one can get from a solar cell, the present invention provides a fifty percent (or better) power transmission efficiency. Therefore, the present invention provides a relatively efficient means of optically transmitting power and data through biological tissue.

FIG. 1 illustrates an internal and external module pair which function together to employ the teachings of the present invention to provide an optical transdermal link. In FIG. 1, internal module 30 has been implanted subdermally such that internal module 30 is surrounded by biological tissue 2. External module 20 is placed with optical transceiver surface 40 adjacent to skin surface 10. Optical transceiver surface 40 is aligned so that it is facing, and substantially parallel to, optical transceiver surface 50 of internal module 30.

In one embodiment of the present invention, power for internal module 20 is supplied from an external power supply (not shown) through a power conduit 12. Similarly, input data to be transmitted from external module 20 to internal module 30 is provided to external module 20 through data conduit 14. Furthermore, output data transmitted from internal module 30 to external module 20 is provided by external module 20 through output data conduit 16 from an external receptacle (not shown).

In one embodiment of the present invention, conduits 12-16 are electrical conduits. However, it will be obvious to one skilled in the art that optical conduits, as well as other types of conduits, could be employed.

In a like manner, power conduit 32 carries power from internal module 30 to a subdermal power drain (not shown) such as a battery or electronic circuitry. Data output conduit 34 provides from internal module 30 the data stream input through data conduit 14 to external module 20. Data conduit 36 provides to internal module 30 the data stream which will be transmitted to external module 20 and subsequently output through output data conduit 16.

In one embodiment of the present invention, data conduits 34 and 36 are coupled to neurons, thereby providing a chronic neural interface. However, it will be obvious to one skilled in the art that data conduits 34 and 36 could alternately receive data from other forms of subdermal transmitters and provide data to other forms of transdermal receivers (e.g. electronic circuitry).

Power is transmitted optically from external module 20 to internal module 30 through a broadly dispersed optical power beam 22. Input data is transferred optically from external module 20 to internal module 30 by way of narrowly dispersed optical beam 24. Similarly, output data is transferred optically from internal module 30 to external module 20 through narrowly dispersed optical beam 26. To reduce interference among the beams, each beam of beams 22-26, operates within the infrared spectrum at a different frequency from each of the other beams 22-26.

Figure 2A:
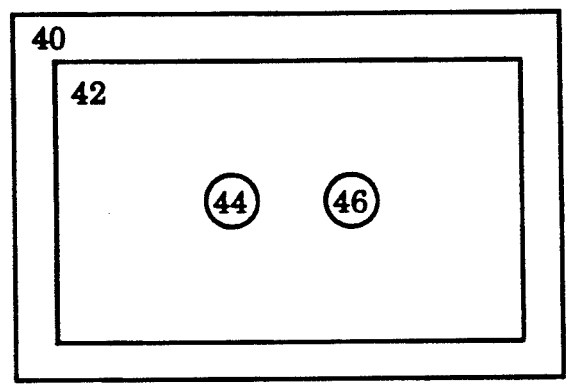
FIG. 2a illustrates an embodiment of an interface surface of an external module of the present invention.

Referring now to FIG. 2a, optical transceiver surface 40 of external module 20 is depicted. Transceiver surface 40 is comprised of three regions. The first region is power transmission region 42. The second region is data transmission region 44 and the third region is data reception region 46.

Figure 2B:
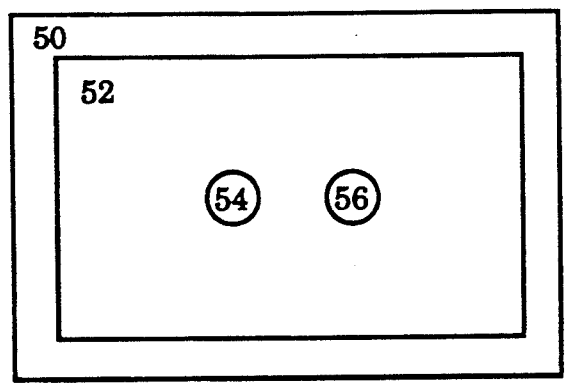
FIG. 2b illustrates an embodiment of an interface surface of an internal module of the present invention.

Referring now to FIG. 2b, optical transceiver surface 50 of internal module 30 is depicted. Transceiver surface 50 is comprised of three regions. The first region is power reception region 52. The second region is data reception region 54 and the third region is data transmission region 56.

Referring now to FIGS. 2a-b jointly, although there are several components located on transceiver surfaces 40 and 50, crowding is not a problem because both modules are constructed using integrated circuit technology. Hence, the solar cell for power reception region 52 would be the only large device on the internal module and, for most purposes, a one square centimeter region would be adequate. On the other hand, the data transmitting and receiving devices tend to be on the order of tens of microns across (i.e. smaller than the diameter of a human hair).

In terms of receiver, one can place on the internal module chip a small photodetector, for bringing data in. This can be done in either of two ways. On the one hand, if one desires a low data rate, it is possible to actually use the power receiver as the data receiver. Thus, for a low data rate, one can modulate the incoming light which is providing power. Up to some modest frequencies, the data could then be read directly from the modulated power beam. However, in some applications, this might not be desirable because it involves modulating the power source, and therefore would complicate the internal module power regulator circuitry.

On the other hand, one could use separate wavelengths for power and data transmission. A photodetector on the implanted chip, tuned to a different infrared wavelength than the wavelength used to transmit power, would detect the data transmission wavelength and therefore be tuned to receive the modulated data signal. Again, the data beam is dispersed so that it will not have to be aligned precisely.

Similarly, data can be brought out through the skin using laser light. A number of new technologies now exist for improving the efficiency of laser diodes. Devices with good performance have been demonstrated to take less than one milliamp of drive current at two volts (i.e. two milliwatts of power). This is a relatively small power consumption. Other devices are down to the level where they draw current on the order of a hundred microamps. The low power consumption of the devices permit one to have a number of transmitting devices on the internal module. Alternately, one could have a single laser diode transmitting data from the internal module and have a number of receiving diodes on the external package.

Again, because the external module is not aligned precisely, one would not focus the transmitted beam down to a tight beam. Instead, one would let the beam spread. By having some knowledge of approximately where one needs to position the external module, the external module would be positioned on the exterior of the skin approximately above the internal module. Whichever of the receiving photodiodes picks up the data transmission signal from the internal unit would then be selected as the one to use to receive the data transmission signal for the internal unit for that particular time that the external coupler is used.

Light emitting diodes (LEDs) are also available that operate in the infrared spectrum. In some applications, LEDs could be employed in the present invention instead of laser diodes. For low data rate applications, using LEDs might be more economical than using laser diodes. However, some of the better laser diodes now available have higher conversion efficiencies than that of a LED.

Figure 3:
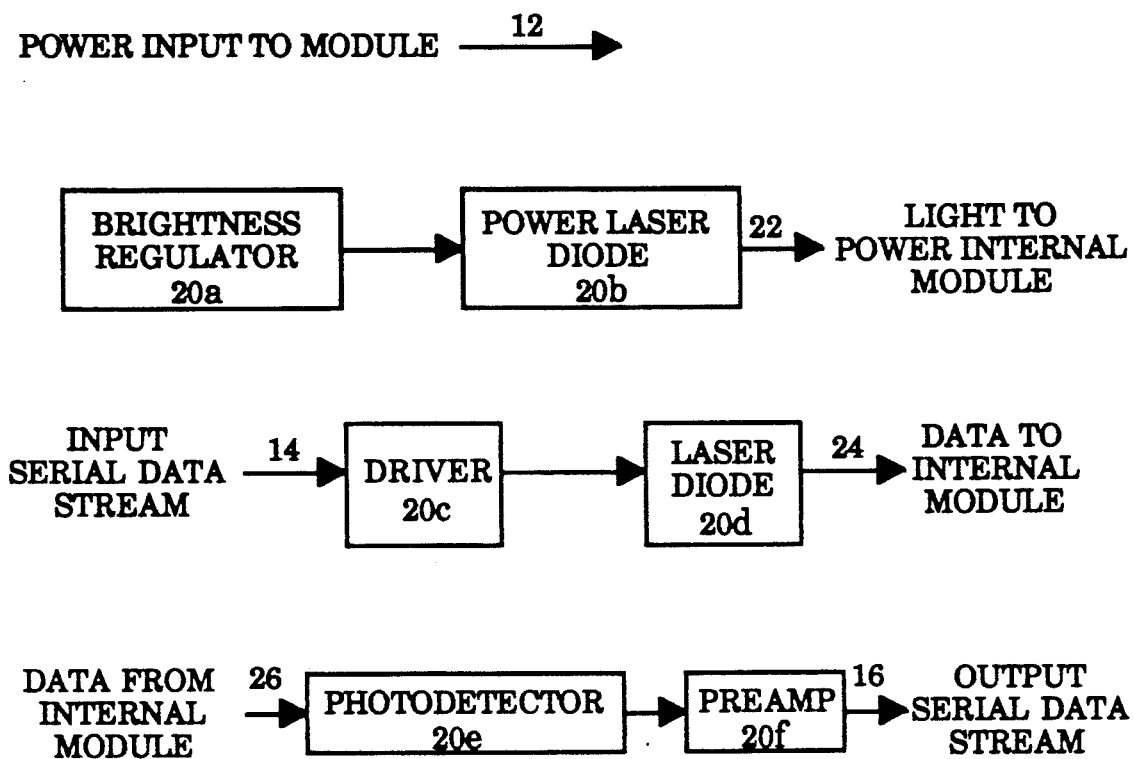
FIG. 3 is a block diagram of an external module of the present invention.

Referring now to FIG. 3, a block diagram of external module 20 is depicted. There are basically three component paths within internal module 20.

The first path is for power. Power is input to external module 20 through power conduit 12 and distributed throughout external module 20 to provide power for component modules 20a-f. Power is also transmitted from external module 20 through broadly dispersed optical beam 22 which is generated by power laser diode 20b. Brightness regulator 20a is coupled to power laser diode 20b and regulates the brightness of diode 20b.

The second path through external module 20 is a data transmission path. An input serial data stream enters external module 20 through data conduit 14 and drives driver 20c. Driver 20c is coupled to laser diode 20d and modulates laser diode 20d so that laser diode 20d produces narrowly dispersed optical beam 24. In this way, the data from conduit 14 is transmitted over beam 24 to the internal module.

In the third path of external module 20, data from beam 26 of the internal module is detected by photodetector 20d and then amplified by preamplifier 20f before being output from external module 20 as a serial data stream through data conduit 16.

Figure 4:
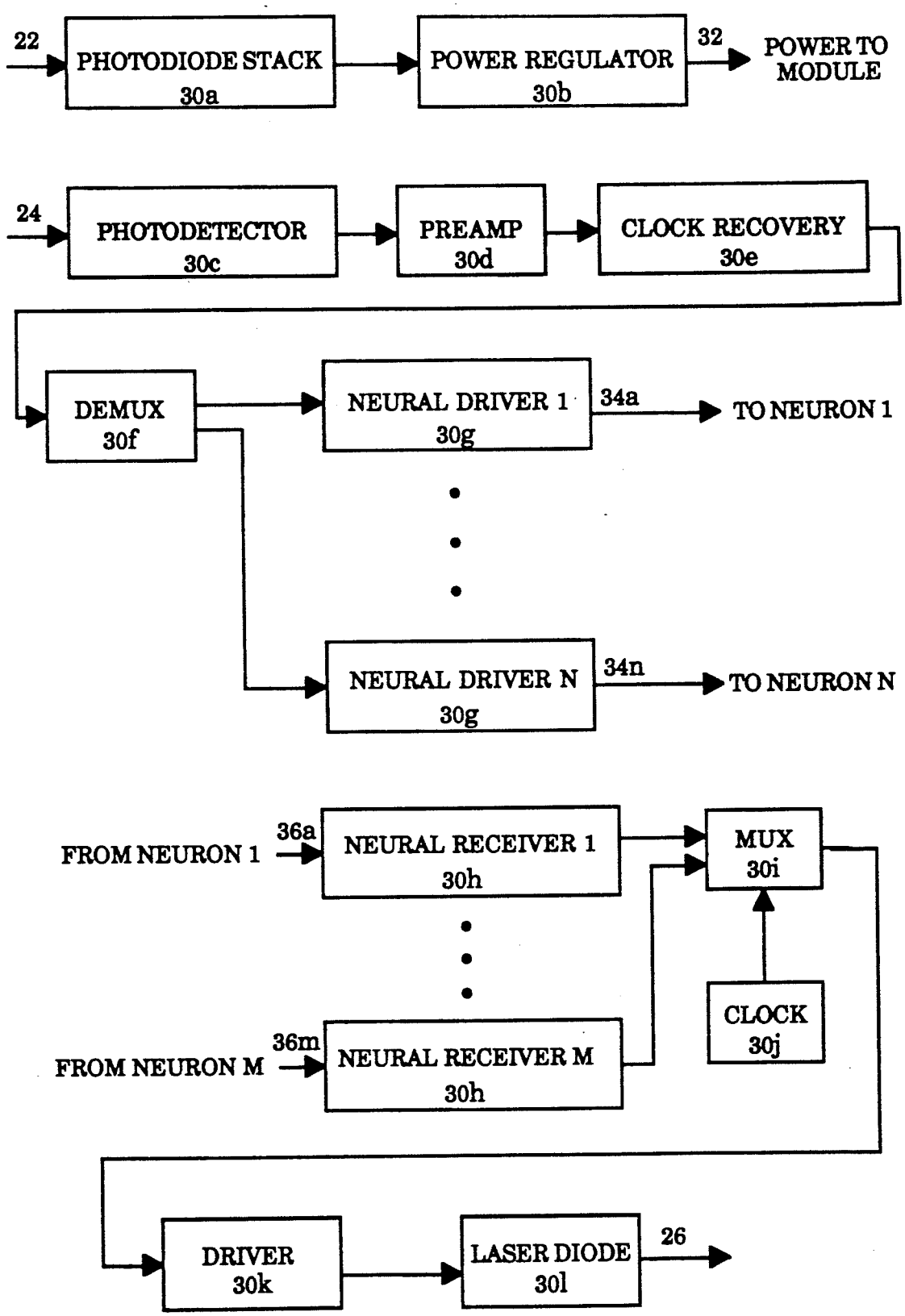
FIG. 4 is a block diagram of an internal module employing the teachings of the present invention.

Referring now to FIG. 4, a block diagram of internal module 30 is depicted. Internal module 30 is comprised of three paths which correspond to the three paths of the external module.

The first path of internal module 30 is a power reception path. Power beam 22 (generated by the external module) is received by photo diode stack 30a and regulated by power regulator 30b. The regulated power is then distributed throughout internal module 30 to power component blocks 30c-l. In one embodiment, regulated power is also carried from internal module 30 by power conduit 32.

In the second path of internal module 30, modulated optical beam 24 (generated by the external module) is detected by photodetector 30c and the resulting signal is amplified by preamplifier 30d. Clock recovery circuitry 30e extracts a clock signal from the incoming data stream and provides the clock signal to demultiplexer circuit 30f. The received data stream then passes through the multiplexer circuit 30f where it is separated into N separate signals. N is a positive integer with a value dependent upon the specific application (e.g. the number of neurons receiving data). Each of the N separate signals are input into a corresponding neural driver 30g. The N neural drivers 30g are coupled to N neurons by conduit 34 such that each neural driver 33 drives a corresponding neuron.

In the third data path of internal module 30, M separate signals are carried to internal module 30 by conduit 36. Here, M is also a positive integer with a value dependent upon the specific application (e.g. the number of neurons providing data). A signal from each of the M neurons is input into a corresponding one of M neural receivers 30h. The M signals output from neural receivers 30h are multiplexed together in multiplexer 30i which is synchronized by clock 30j to provide a single transmission data stream that controls driver 30k. Driver 30k modulates laser diode 30l thereby causing the multiplexed data stream from the M neurons to be emitted by laser diode 30l and transmitted over optical beam 26 to the external module.

Preferably a single clock drives both the internal and external modules. If multiple clocks are used, some sort of synchronization must be performed. For instance, if there is only a data link out of internal module 30 (i.e., no input data link), the internal clock 30j could simply be a free running oscillator.

Alternately, "self-clocking" circuits, well known in the art of telecommunications and which use techniques such as Manchester coding can be used. These self-clocking circuits permit the internal module to recover an external clock signal by reading the data signal received from the external module. For example, in Manchester coding, both data and timing signals are combined into a single stream of transmitted bits. The data value of each bit is indicated by the signal state (e.g. high for 1, low for 0) during the first half of a bit period (time required to define a single bit). A transmission to the opposite state at the middle of the bit period acts as a timing signal. Therefore, there is no need to have a separate clock channel between the external and internal modules.

Furthermore, in an alternate embodiment of the present invention, clock recovery circuit 30e provides the clock signal for multiplexer 30i thereby synchronizing the two systems and eliminating the need for clock 30j.

In another embodiment of the present invention, the external device has additional electronics in it to generate the data stream transmitted from the external module and to process the data stream which the external module receives from the internal module.

Alternately, in another embodiment of the present invention, the external module only contains fiber optics and optical elements to spread out the power and data transmission beams. In this embodiment, all the data generation and processing electronics are located remotely at the end of a fiber optic cable. The external module is therefore a very simple generic device. The part that contains the electronics for the external module is designed on an ad hoc basis to meet the requirements of a particular application.

To position the external module and hold it in place, the external module is simply strapped into place using a variety of techniques well known in the art. Alternately, one can position the external module on an ear lobe as though it is a pierced earring. Thus, if a shunt in the area of the ear is required, the internal module is placed within the ear lobe. Alternately, the neural interface can be located at some distance from the optical interface by means of a small electrical cable or flex circuit. The external module is affixed to the ear lobe using double posts and retainer clips, as one would affix a pierced earring. To do so provides a very good alignment of the internal and external modules.

Figure 5:
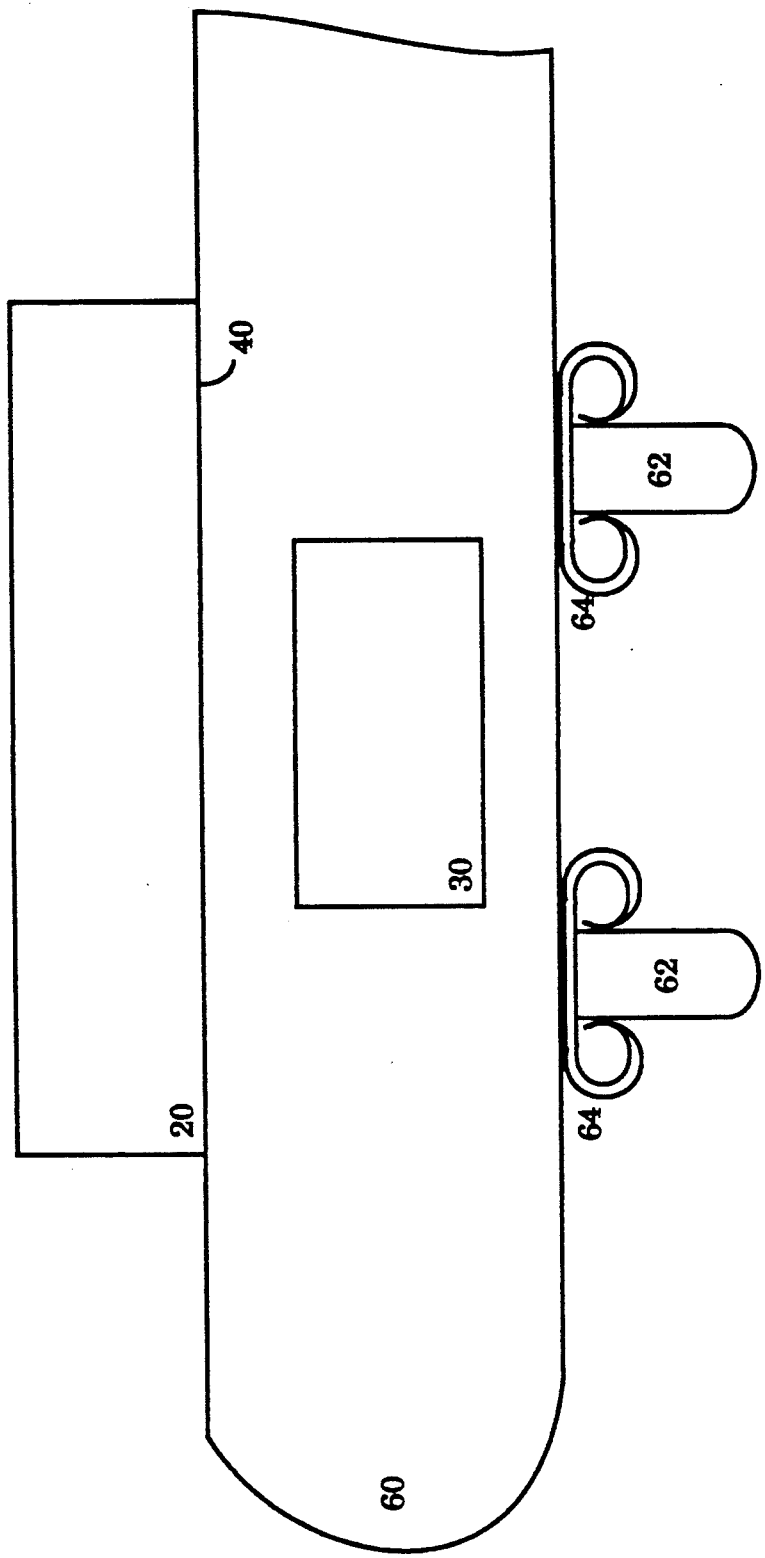
FIG. 5 illustrates an alternate embodiment optical transdermal link which employs the teachings of the present invention.

Referring now to FIG. 5, an alternate embodiment of the present invention is illustrated which positions the external module as though the external module is a pierced earring. In FIG. 5, internal module 30 has been implanted within double-pierced earlobe 60. External module 20 has two earring posts 62 affixed to optical transceiver surface 40. The pair of earring posts 62 are spaced to correspond to a pair of pierced holes in lobe 60. Internal module 30 is placed within lobe 60 such that it is properly aligned with external module 20 when earring posts 62 have been inserted into the pierced holes of lobe 60. Retention clips 64 attach to earring posts 62 and thereby hold external module 20 in place on lobe 60 such that external module 20 is properly aligned with internal module 30.

Thus, one can wear a fairly elegant looking earring (not shown) with a fiber (not shown) running quite inconspicuously to external module 20 embedded within the earring. In this way, an aligned, yet unobtrusive, chronic neural link is provided.

Furthermore, it will be obvious to one skilled in the art that the present invention does not have to provide a bi-directional data link. The link is used to transmit data unidirectionally. The link also is used solely to transmit power. Moreover, it is obvious that, in an alternate embodiment of the present invention, the link is used to exclusively transmit data (unidirectionally or bi-directionally).

Optical telecommunications devices routinely operate over great distances at data transmission rates of a gigabit per second or higher. However, while the present invention provides data transmission rates in the order of a gigabit per second, there currently are few prosthetic applications that require such high data transmission rates. Still, a gigabit per second is approximately the bandwidth of an optic nerve. Thus, as the technology for interfacing with nerves improves, the present invention can be used to provide the power and data that will allow one to replace, for instance, a missing eye.

Moreover, as the technology for interfacing with nerves improves, interfaces to the optic nerve can be utilized to provide taps into the nervous system and thereby bypass the screens of computers. In this way, computer information can be added to a visual stream. In fact, other sensory streams can be tapped, thereby providing a complete sensory experience which would be useful for various kinds of simulation work.

The present invention has application for use in subdermal optical energy and power transmission environments and may be incorporated into a variety of systems for transmitting power or data through biological tissue. Although the present invention has been described in conjunction with the embodiments illustrated in FIGS. 1-5, it is evident that numerous alternatives, modifications, variations and uses will be apparent to those skilled in the art in light of the foregoing description.

What is claimed is:

1. An apparatus comprising:
   an internal module to be embedded within biological tissue; and
   an external module located external to the biological tissue;
   the external module comprising:
      an external optical transmission means;
      an external driver coupled to the external optical transmission means, the external driver for receiving a first data stream and modulating the external optical transmission means according to the first data stream thereby driving the external optical transmission means and causing the external optical transmission means to transmit a modulated first data stream optical signal;
   the internal module comprising:
      a photo array for receiving the modulated first data stream optical signal from the external optical transmission means and converting the modulated first data stream optical signal into a first data stream modulated electrical signal;
      power extraction means, coupled to the photo array for extracting power from the modulated first data stream electrical signal;
      internal signal extraction means coupled to the photo array and extracting the first data stream from the modulated first data stream electrical signal;
      an internal optical transmission means coupled to and powered by the power extraction means;
      an internal driver coupled to and powered by the power extraction means, and further coupled to the internal optical transmission means, the internal driver for receiving a second data stream and modulating the internal optical transmission means according to the second data stream thereby driving the internal optical transmission means and causing the internal optical transmission means to transmit a modulated second data stream optical signal;
   the external module further comprising:
      an external optical reception means for receiving the modulated second data stream optical signal and converting the modulated second data stream optical signal into a second data stream modulated electrical signal;
      external signal extraction means coupled to the external optical reception means for extracting the second data stream from the modulated second data stream electrical signal.

2. The apparatus as set forth in claim 1 wherein the first data stream is provided by a host processor coupled to the external driver by a first high speed serial line and the second data stream is provided to the host processor by a second high speed serial line.

3. The apparatus as set forth in claim 1 wherein the second data stream is provided to the internal driver by a neural interface circuit that is coupled to a neuron and receives the second data stream from the neuron and the first data stream is provided to the neural interface circuit for reception by the neuron.

4. The apparatus as set forth in claim 1 wherein the first data stream is comprised of a plurality of first data signals multiplexed according to an external clock signal to form the first data stream and wherein the internal module further comprises:
- a clock recovery means coupled to the internal signal extraction means for extracting the external clock signal from the first data stream; and
- a demodulation unit coupled to the clock recovery means and to the internal signal extraction means for decomposing the first data stream into the plurality of first data signals.

5. The apparatus as set forth in claim 4 wherein there are a plurality of neurons and a corresponding plurality of neural interfaces such that each neural interface is coupled to a neuron and wherein each first data signal is provided to a corresponding neural interface for providing the corresponding first data signal to the neuron coupled thereto.

6. The apparatus as set forth in claim 5 wherein there is a plurality of second data signals and wherein the internal module further comprises:
- a multiplexing unit coupled to the clock recovery means and to the internal driver for composing the first data stream from the plurality of first data signals, each of the neural interfaces provides a second data signal of the plurality of second data signals, the plurality of second data signals being multiplexed by the multiplexing unit according to the external clock signal to form the second data stream.

7. The apparatus as set forth in claim 1 wherein the external module comprises a plurality of external optical signal reception means and the external optical signal reception means best aligned with the internal optical transmission means is selected to provide the modulated first data stream electrical signal to the internal signal extraction means.

8. The apparatus as set forth in claim 1 wherein the biological tissue is part of an ear lobe and the external module further comprises:
- at least two earring posts extending through the ear lobe;
- at least two retainer clips, there being a retainer clip of the retainer clips for each of the earring posts, the retainer clips being attached to the earring posts and thereby holding the external module in a position with respect to the internal module such that the photo array will receive the modulated first data stream optical signal and the external optical reception means will receive the modulated second data stream optical signal.

9. An apparatus comprising:
- an internal module to be embedded within biological tissue; and
- an external module located external to the biological tissue;
- the external module comprising:
  - an external optical power transmission means for transmitting optical power;
  - an external optical signal transmission means;
  - an external driver coupled to the external optical signal transmission means, the external driver for receiving a first data stream and modulating the external optical signal transmission means according to the first data stream thereby driving the external optical signal transmission means and causing the external optical transmission means to transmit a modulated first data stream optical signal;
- the internal module comprising:
  - a photo array for receiving the transmitted optical power from the external optical power transmission means and converting the transmitted optical power into electrical power;
  - an internal optical reception means for receiving the modulated first data stream optical signal and converting the modulated first data stream optical signal into a first data stream modulated electrical signal; internal signal extraction means coupled to the internal optical reception means and for extracting the first data stream from the modulated first data stream electrical signal;
  - an internal optical transmission means coupled to and powered by the photo array;
  - an internal driver coupled to and powered by the photo array, and further coupled to the internal optical transmission means, the internal driver for receiving a second data stream and modulating the internal optical transmission means according to the second data stream thereby driving the internal optical transmission means and causing the internal optical transmission means to transmit a modulated second data stream optical signal;
- the external module further comprising:
  - an external optical reception means for receiving the modulated second data stream optical signal and converting the modulated second data stream optical signal into a second data stream modulated electrical signal;
  - external signal extraction means coupled to the external optical reception means for extracting the second data stream from the modulated second data stream electrical signal.

10. The apparatus as set forth in claim 9 wherein the first data stream is provided by a host processor coupled to the external driver by a first high speed serial line and the second data stream is provided to the host processor by a second high speed serial line.

11. The apparatus as set forth in claim 10 wherein the first data stream is comprised of a plurality of first data signals multiplexed according to an external clock signal to form the first data stream and wherein the internal module further comprises:
- a clock recovery means coupled to the internal signal extraction means for extracting the external clock signal from the first data stream; and
- a demodulation unit coupled to the clock recovery means and to the internal signal extraction means for decomposing the first data stream into the plurality of first data signals.

12. The apparatus as set forth in claim 11 wherein there are a plurality of neurons and a corresponding plurality of neural interfaces such that each neural interface is coupled to a neuron and wherein each first data signal is provided to a corresponding neural interface for providing the corresponding first data signal to the neuron coupled thereto.

13. The apparatus as set forth in claim 12 wherein there is a plurality of second data signals and wherein the internal module further comprises:
- a multiplexing unit coupled to the clock recovery means and to the internal driver for composing the first data stream from the plurality of first data signals, each of the neural interfaces provides a second data signal of the plurality of second data signals, the plurality of second data signals being multiplexed by the multiplexing unit according to the external clock signal to form the second data stream.

14. The apparatus as set forth in claim 9 wherein the second data stream is provided to the internal driver by a neural interface circuit that is coupled to a neuron and receives the second data stream from the neuron and the first data stream is provided to the neural interface circuit for reception by the neuron.

15. The apparatus as set forth in claim 9 wherein the internal module comprises a plurality of internal optical signal reception means and the internal optical signal reception means best aligned with the external optical transmission means is selected to provide the modulated first data stream electrical signal to the internal signal extraction means.

16. The apparatus as set forth in claim 9 wherein the external module comprises a plurality of external optical signal reception means and the external optical signal reception means best aligned with the internal optical transmission means is selected to provide the modulated first data stream electrical signal to the internal signal extraction means.

17. The apparatus as set forth in claim 9 wherein the biological tissue is part of an ear lobe and the external module further comprises:
   at least two earring posts extending through the ear lobe;
   at least two retainer clips, there being a retainer clip of the retainer clips for each of the earring posts, the retainer clips being attached to the earring posts and thereby holding the external module in a position with respect to the internal module such that the photo array will receive the transmitted optical power, the internal optical reception means will receive the modulated first data stream optical signal and the external optical reception means will receive the modulated second data stream optical signal.

* * * * *